United States Patent [19]
Castanis et al.

[11] 4,335,067
[45] Jun. 15, 1982

[54] PRODUCING REPLICAS OF BODY PARTS

[76] Inventors: George Castanis; Thaddeus T. Castanis, both of 444 6th Ave., New York, N.Y. 10011

[21] Appl. No.: 263,349

[22] Filed: May 13, 1981

[51] Int. Cl.³ .............................................. B29C 1/02
[52] U.S. Cl. .................................. 264/222; 264/225; 264/DIG. 30; 264/337
[58] Field of Search ....... 264/222, 223, 225, DIG. 30, 264/337

[56] References Cited
U.S. PATENT DOCUMENTS

| | | | |
|---|---|---|---|
| 2,249,694 | 7/1941 | Wilding . | |
| 2,473,723 | 6/1949 | Nelson | 264/DIG. 30 |
| 2,508,156 | 5/1950 | Gillman | 264/222 |
| 2,996,757 | 8/1961 | Heflin | 264/DIG. 30 |
| 3,010,834 | 11/1961 | Crowell | 106/38.4 |

*Primary Examiner*—James B. Lowe
*Attorney, Agent, or Firm*—Michael Ebert

[57] ABSTRACT

A molding kit to facilitate the synthetic cloning of body parts, such as fingers, the kit including a supply of alginate powder and a mold form having a bottom opening that is sealed when the form is seated on a base. A charge of powder is mixed with water to form a quick-setting, flowable molding compound. This is poured into the mold form, after which the body member is inserted and held therein until the compound sets to form an elastic gel. The gel is then pushed out of the mold form through the bottom opening, and the body part withdrawn to expose the impression cavity. The gel is returned to the mold form which is again seated and a flowable casting compound of the same composition as the molding compound is poured into the cavity and permitted the set to create a flesh-like clone of the body part. This clone is readily removable from the cavity without marring the impression therein.

7 Claims, 6 Drawing Figures

PRODUCING REPLICAS OF BODY PARTS

BACKGROUND OF INVENTION

This invention relates generally to molding techniques, and in particular to a kit making it possible for a user to quickly reproduce a part of his body, such as a finger, and to create a "clone" thereof having flesh-like properties.

In a strict scientific sense, a clone refers to all individuals, considered collectively, produced asexually or by parthenogenesis from a single individual. In recent years, however, because of best-selling novels, motion pictures and T-V presentations dealing with cloning on a science fiction or pseudo-science level, the term "clone" has entered the common parlance and is generally taken to mean a copy of an individual or a part thereof, whether in living or inanimate form.

The widespread concern with cloning and the theoretical possibility that future generations may be composed of cloned rather than sexually reproduced individuals has inspired an interest in reproducing parts of the body by molding techniques. In this way one could, for example, make a reasonably good copy of a person's ear, finger or other body component.

While known molding and casting techniques may, of course, be employed to provide a plastic or metal copy of any body part, these techniques are all relatively elaborate and costly, and they do not lend themselves to simple cloning operations, particularly in the hands of children. Moreover, parts molded by conventional technique are generally rigid and lacking in flesh-like properties.

SUMMARY OF INVENTION

In view of the foregoing, the main object of this invention is to provide a simple, inexpensive and safe technique for synthetically cloning parts of the body or other pieces to produce copies having flesh-like characteristics. The term synthetic clone as used herein refers to a clone that is fleshlike, but is not an actual clone in the scientific sense.

More particularly, an object of this invention is to provide a technique of the above type in which an elastic gel compound is used to make an impression of the body member to be cloned, the same compound being used to produce a flesh-like casting of the body member.

A significant feature of the invention is that it is not necessary to break the mold to remove the casting therefrom, the same mold being reusable to produce additional castings.

Also an object of the invention is to provide a low-cost kit to facilitate the synthetic cloning of body parts and other pieces.

Briefly stated, these objects are attained in a molding kit to facilitate the synthetic cloning of body parts, such as fingers, the kit including a supply of alginate powder and a mold form having a bottom opening which is sealed when the form is seated on a base. A portion of the powder is mixed with water to form a quicksetting, flowable molding compound. This is poured into the mold form, after which the body member is inserted and held therein until the compound sets to form an elastic gel. The gel is then pushed out of the mold form through the bottom opening, and the body part withdrawn to expose the impression cavity. The gel is returned to the mold form which is again seated, and a flowable casting compound of the same composition as the molding compound is poured into the cavity and permitted to set to create a flesh-like clone of the body part which is readily removable from the cavity without marring the impression therein.

OUTLINE OF DRAWINGS

For a better understanding of the invention as well as other objects etc.

Figure 5:
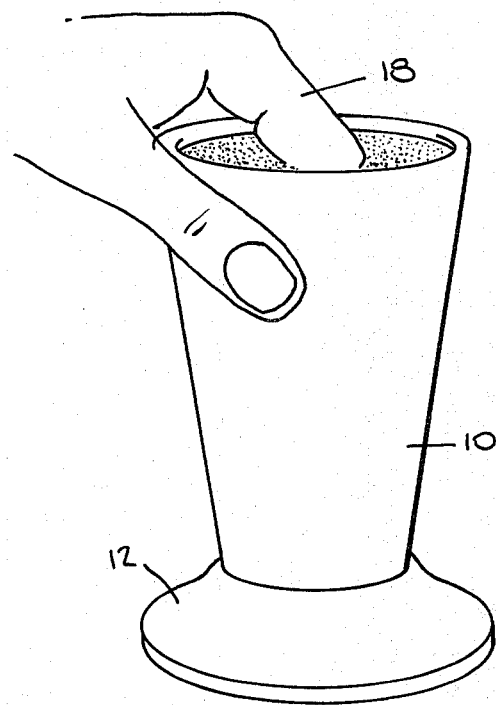
Figure 2:
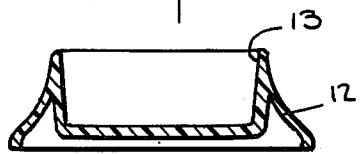
FIG. 2 is a sectional view of the removable base for the mold form.
Figure 6:
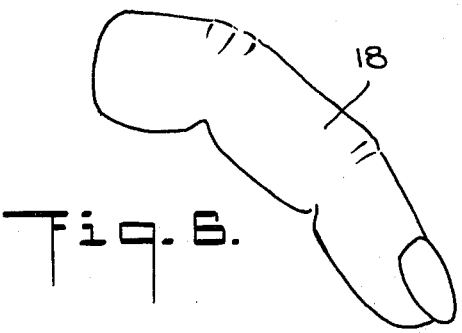
Figure 4:
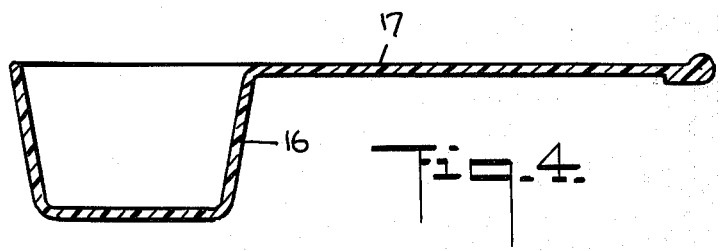
FIG. 4 is a section taken through a measuring cup and stirring tool included in the kit.

FIG. 5, in perspective, shows the mold form seated on the base, with a finger inserted in the molding compound, and FIG. 6 shows the cast finger.

DESCRIPTION OF INVENTION

In a kit in accordance with the invention, an alginate powder is used to produce not only a flowable molding compound which is quick setting, but is also used as the casting compound.

Alginates are used as an impression material in dentistry. Irreversible hydrocolloids, more commonly called alginates, were developed during World War 11, the alginates being salts of alginic acid obtained from marine kelp. The alginates change from the sol to the gel form by an irreversible chemical reaction. The sol form is always a soluble salt of alginic acid, whereas the gel is an insoluble salt.

The essential constituents of alginate impression powders are the soluble alginate, a reactor such as calcium sulfate and a retarder such as trisodium phosphate. When this powder is mixed with water, all three ingredients proceed to dissolve. The retarder, however, ties up the reactor for a short time so that the reactor is not available to convert the soluble alginate to an insoluble gel. As soon as the retarder has been spent, gelation begins throughout the powderwater mixture. Among the patents disclosing alginate impression compounds are the Crowell U.S. Pat. Nos. 3,010,834 and the Wilding 2,249,694.

As noted in The American Dental Association specification No. 18, effective 1969, "for alginate impression material," this material must be compatible with gypsum, which is the plaster used to make dental castings. By compatibility, the Association means that the alginate impression shall impart a smooth, non-chalky surface to and "separate cleanly from a gypsum cast."

The setting time of commercially-available alginate impression materials depends on whether it has normal or fast setting characteristics, but it ranges from about 60 to 120 seconds to no more than about 4 minutes. For the present invention, the preferred setting time is about 3 minutes.

We have discovered that it is possible to use, instead of gypsum or other conventional casting material which produces a hard cast, a casting material which is of the same composition as the alginate used in the molding material, and that as long as this unique casting material is poured into the impression cavity after the alginate mold has fully gelled, the resultant casting, even though it is also a gelled alginate, separates cleanly from the alginate mold. The mold, therefore, is reusable.

Figure 1:
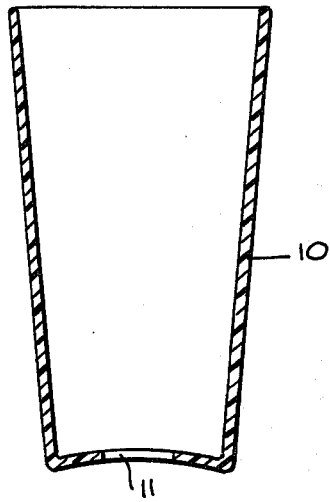
FIG. 1 is a section taken through a cylindrical mold form included in a kit for cloning parts in accordance with the invention.

To exploit this discovery, a kit in accordance with the invention makes use of a mold form 10, as shown in FIG. 1. Since it is intended in this example to synthetically clone a single finger of an individual, the mold form has a slightly tapered cylindrical form, the bottom of the mold form having an opening 11 therein. The dimensions of this mold form are adequate to receive a single finger. It is to be understood, however, that when other body parts are to be cloned, such as feet or hands, the mold form will have dimensions appropriate thereto. It is also possible to provide mold forms for articles such as small dolls which can be reproduced into a form which is flesh-like.

Mold form 10 is seatable on a base 12 having a shell 13 integral therewith, which defines a socket to receive the form and thereby provide a stable base therefor, the base sealing bottom opening 11 in the seated mold form.

Figure 3:
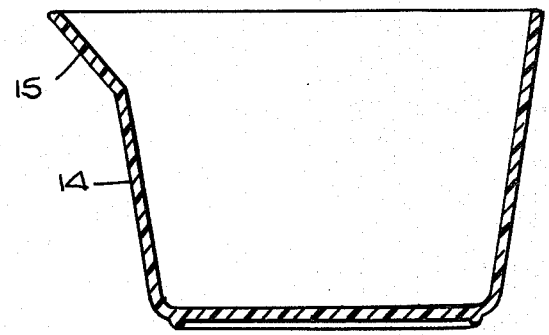
FIG. 3 is a section of the mixing and pouring bowl included in the kit.

A supply of alginate powder is provided. And for this purpose, the supply may be in a single large cannister or in multiple sealed packets, each containing a single charge. In order to mix the powder with water in the ratio prescribed by the supplier of the powder, such as one part powder to two parts water, a mixing bowl 14 is provided. As shown in FIG. 3, bowl 14 has a pouring spout 15. The amount of powder used to produce the molding compound must be no more than necessary to fill mold from 10, and for this purpose a measuring cup 16 is provided to hold the proper amount of powder, the cup having an extended handle 17 which also functions as a stirring tool.

Thus one ladles out from the supply with the measuring cup the proper amount of alginate powder, the powder being poured into bowl 14, after which a suitable amount of water is added and the mixture stirred with handle 17 until it has a uniform consistency.

The alginate molding compound is then poured into seated mold form 10 to a level close to the top, after which the finger 18 to be cloned, as shown in FIG. 5, is inserted into a molding compound. The finger is held therein for a minute or more, depending on the setting time of the compound. When the compound has fully gelled, the base is removed from the mold form, and the gel is pushed out by holding the mold form in one hand, and inserting a finger of the other hand through opening 11.

Then the finger is withdrawn from the gel to expose the cavity therein which contains the finger impression. The gel mold is placed back in the seated mold form, and this time a small amount of alginate mixed with water is prepared in the mixing bowl to produce enough casting compound to fill the cavity.

It is important to note that even though the casting compound is identical to the molding compound, because of its relatively short setting time, one cannot prepare both the molding and casting compounds in a single batch; for by the time one is ready to use the casting compound, it would have gelled. Hence the casting compound must be prepared only after the gelled impression is created.

When the casting compound in the cavity has gelled, the gelled mold having the gelled casting therein is removed from the mold form. The casting has the same color and elasticity as the mold, so that to all appearances one has an integrated block of gelled alginate. However, the gelled casting does not adhere to the cavity wall and the elastic casting is readily separable from the elastic mold and can be gently pushed out without in any way mutilating the impression. Thus the impression is reusable to create additional gelled castings.

The resultant clone 18 of the finger, as shown in FIG. 6, because it is constituted by an elastic gel, has flesh-like properties, particularly since the alginate used is of the type normally employed to make dental impressions and is flesh-toned.

While there has been shown and described a preferred embodiment of Synthetic Cloning Technique in accordance with the invention, it will be appreciated that many changes and modifications may be made therein without, however, departing from the essential spirit thereof.

We claim:

1. A method of synthetically cloning a body part or other member to produce a replica thereof having flesh-like properties, the method comprising the steps of:
    A mixing a charge of alginate powder taken from a supply thereof with water to produce a quick-setting flowable molding compound;
    B pouring the molding compound into a mold form and inserting the part to be cloned therein to create an impression cavity:
    C holding the inserted part in the compound until it has gelled, the part then being removed to expose the impression cavity in the gelled mold;
    D mixing a charge of alginate powder taken from a supply thereof with water to produce a quick-setting casting compound;
    E pouring the casting compound into the cavity; and
    F after the casting compound has gelled to form the replica, removing it from the cavity.

2. The method as set forth in claim 1 wherein the molding and casting compounds have the same composition, yet the replica is separable from the mold.

3. The method as set forth in claim 1, wherein said mixing steps are carried out in a mixing bowl having a spout to facilitate pouring of the resulting compound.

4. The method as set forth in claim 1, wherein said setting time is about two minutes.

5. The method as set forth in claim 1, wherein said part is a finger and said mold form is cylindrical and dimensioned to receive said finger.

6. The method as set forth in claim 5, wherein said mold form has a bottom opening which is sealed when the form is seated on a base, said opening facilitating the removal of the gelled mold from the form.

7. The method as set forth in claim 3, wherein said charge of alginate powder is measured by a measuring cup which has an extended handle usable to effect said mixing in said bowl.

* * * * *